United States Patent
LaVoie et al.

(10) Patent No.: US 9,695,135 B2
(45) Date of Patent: Jul. 4, 2017

(54) THERAPEUTIC CATECHOLS

(71) Applicant: RUTGERS, THE STATE UNIVERSITY OF NEW JERSEY, New Brunswick, NJ (US)

(72) Inventors: Edmond J. LaVoie, New Brunswick, NJ (US); Eddy Arnold, New Brunswick, NJ (US); Joseph D. Bauman, New Brunswick, NJ (US); John E. Kerrigan, New Brunswick, NJ (US); Ajit K. Parhi, New Brunswick, NJ (US); Kalyan Das, New Brunswick, NJ (US); Cody Kelley, New Brunswick, NJ (US); Dishaben V. Patel, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/709,108

(22) Filed: May 11, 2015

(65) Prior Publication Data
US 2015/0322022 A1 Nov. 12, 2015

Related U.S. Application Data

(60) Provisional application No. 61/992,070, filed on May 12, 2014.

(51) Int. Cl.
| | |
|---|---|
| *C07D 257/04* | (2006.01) |
| *C07C 205/22* | (2006.01) |
| *C07C 255/53* | (2006.01) |
| *C07C 39/15* | (2006.01) |
| *C07C 39/367* | (2006.01) |
| *C07C 205/26* | (2006.01) |

(52) U.S. Cl.
CPC ............ *C07D 257/04* (2013.01); *C07C 39/15* (2013.01); *C07C 39/367* (2013.01); *C07C 205/22* (2013.01); *C07C 205/26* (2013.01); *C07C 255/53* (2013.01)

(58) Field of Classification Search
None
See application file for complete search history.

(56) References Cited

U.S. PATENT DOCUMENTS

2013/0245049 A1* 9/2013 Chaltin ............... C07D 221/06
514/267

FOREIGN PATENT DOCUMENTS

JP 2010248111 * 11/2010 ........... A61K 31/166

OTHER PUBLICATIONS

Machine translation of JP 2010248111, obtained from <https://dossier1.j-platpat.inpit.go.jp/tri/all/odse/ODSE_GM101_Top.action>, Accessed Feb. 19, 2016.*
Hu et al., Chinese Journal of Chemistry, 2012, 30, 2752-2758.*
Himmel, et al., "Structure of HIV-1 reverse transcriptase with the inhibitor beta-Thujaplicinol bound at the RNase H active site", Structure 17 (12), 1625-1635 (2009).
Locatelli, et al., "Diketo hexenoic acid derivatives are novel selective non-nucleoside inhibitors of mammalian terminal deoxynucleotidyl transferases, with potent cytotoxic effect against leukemic cells", Mol Pharmacol 68 (2), 538-550 (2005).
Nadal, et al., "Structure and inhibition of herpesvirus DNA packaging terminase nuclease domain", Proc Natl Acad Sci 107 (37), 16078-16083 (2010).
Zhang, et al., "HIV-1 Integrase Inhibitor-Inspired Antibacterials Targeting Isoprenoid Biosynthesis", ACS Med Chem Lett 3 (5), 402-406 (2012).

* cited by examiner

*Primary Examiner* — Alicia L Otton
(74) *Attorney, Agent, or Firm* — Viksnins Harris & Padys PLLP

(57) ABSTRACT

The invention provides compounds of formula I:

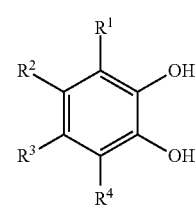

and salts thereof wherein $R_1$-$R_4$ have any of the meanings defined in the specification, as well as pharmaceutical compositions comprising the compounds or salts, and methods for their use in therapy. The compounds have useful antiviral properties.

16 Claims, No Drawings

SEQUENCE LISTING

<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic probe

<400> SEQUENCE: 1
tggcaatatc agctccaca                                                19

THERAPEUTIC CATECHOLS

PRIORITY OF INVENTION

This application claims priority from U.S. Provisional Application No. 61/992,070, filed May 12, 2014. The entire content of this provisional application is hereby incorporated herein by reference.

SEQUENCE LISTING

The instant application contains a Sequence Listing which has been submitted electronically in ASCII format and is hereby incorporated by reference in its entirety. Said ASCII copy, created on Jul. 24, 2015, is named 00435.004US1_SL.txt and is 636 bytes in size.

BACKGROUND OF THE INVENTION

Influenza A infects a wide range of avian and mammalian hosts. The constant ability of the virus to evolve requires reformulation of seasonal influenza vaccines on a yearly basis. The virus has eight genomic RNA segments; reassortment of genomic RNAs from different strains and subtypes of influenza A is responsible for sporadic emergence of pandemic flu (Palese, P.; Shaw, M. L. Orthomyxoviridae: The Viruses and Their Replication. In Fields Virology, 5th ed., 2001; and Knipe, D. M., Howley, P. M., Eds.; Lippincott Williams & Wilkins: Philadelphia, Pa., 2007; Vol. 2, pp 1647-1689). Alternatively, all eight genomic RNAs may be derived from an avian virus, and such a progenitor virus then undergoes multiple mutations in the process of adapting to a mammalian host (Taubenberger et al., Nature. 2005; 437(7060): 889-93).

Antivirals are used for both prophylactic and therapeutic treatments of influenza infection. The available treatment options for influenza are limited. Current antivirals are directed against the M2 ion-channel protein (adamantanes) and neuraminidase (zanamivir and oseltamivir). The adamantane drugs, amantadine and rimantadine, are ineffective due to emergence of resistance (predominantly through a M2 mutation, S31N) and these drugs, in general, are not in clinical use. The neuraminidase (NA)-inhibiting oral drug, oseltamivir (Tamiflu) is widely used for treating flu. Oseltamivir-resistant seasonal influenza A strains have been circulating for several years (Moscona, N Engl J Med. 2005; 353(25):2633-6). The mutant viruses predominantly contain the NA H274Y mutation. When accompanied by compensatory mutations, the mutant viruses exhibit fitness comparable to wild-type influenza A and remain resistant to oseltamivir (Bloom et al., Science. 2010; 328(5983): 1272-5). These mutations can emerge in almost all influenza A subtypes/strains, including the pandemic 2009 H1N1 virus (Memoli et al., J Infect Dis. 2011; 203(3):348-57), resulting in a major concern for an effective treatment of flu. Therefore, new drugs are essential for treating drug-resistant and future pandemic flu strains.

Influenza A contains eight negative-stranded RNA genomic segments. The three largest genomic RNA segments encode the viral RNA-dependent RNA polymerase (RdRP) proteins consisting of the polymerase acidic protein (PA) and polymerase basic protein 1 (PB1) and 2 (PB2) subunits. The PA subunit: (i) has endonuclease activity (ii) is involved in viral RNA (vRNA)/complementary RNA (cRNA) promoter binding, and (iii) interacts with the PB1 subunit (reviewed by Das et al., Nat Struct Mol Biol. 2010; 17(5):530-8). PA has two domains, $PA_N$ (a ~25 kDa N-terminal domain; residues 1-197) and $PA_C$ (~55 kDa C-terminal domain; residues 239-716). Crystal structures of $PA_C$ have been determined in complexes with N-terminal fragments of PB1 (He et al., Nature. 2008; 454(7208): 1123-6).

The RdRP of influenza A is responsible for the replication and transcription of the viral RNA genes. The viral mRNA transcription involves a cap-snatching mechanism in which the polymerase binds to cellular mRNA via the 5'-cap and cleaves the mRNA 12-13 nucleotides downstream. The cleaved RNA fragment containing the 5' cap acts as a primer for viral mRNA synthesis (Plotch et al., Cell. 1981; 23(2): 847-58). Cap-snatching is an important event in the life cycle of all members of the Orthomyxoviridae family including influenza A, B and C viruses, and the host cell has no analogous activity. Therefore, inhibitors of cap-snatching would act against all influenza subtypes and strains, including tamiflu-resistant influenza A viruses, and will not interfere with host cell activities.

The complete structure of the viral polymerase has not yet been determined at atomic resolution; however, recent structural studies of parts of the influenza A polymerase (reviewed by Das et al., Nat Struct Mol Biol. 2010; 17(5):530-8) have begun to elucidate the architecture of this complex and started to identify multiple promising target sites for designing new influenza drugs. The crystal structures of the N-terminal domain of PA subunit ($PA_N$) from H5N1 (Yuan et al., Nature. 2009; 458(7240):909-13) and H3N2 (Dias et al., Nature. 2009; 458(7240):914-8) viruses established that the $PA_N$ domain contains the endonuclease active site composed of conserved acidic residues E80, D108, and E119 positioned in a deep cleft. Blocking the binding of host mRNAs to the cleft and/or inhibiting the cleavage of the host mRNAs would inhibit the synthesis of the viral mRNAs and thereby, inhibit replication of influenza A.

The $PA_N$ domain of 2009 pandemic H1N1 virus polymerase (residues 1-204) has now been crystallized in three distinct forms (U.S. patent application Ser. No. 13/554,709). These new crystal forms provide for the determination of 3-dimensional structures of $PA_N$ with endonuclease inhibitors. In addition, a high-throughput methodology (U.S. patent application Ser. No. 13/554,709) has been developed and optimized for screening compounds to inhibit influenza endonuclease. Additional crystal forms of $PA_N$, suitable for structure based drug design, have recently been reported by Kowalinski et al. (PLOS Pathogens. 2012; 8(8):e1002831) using a 2009 pandemic H1N1 sequence and by Dubois et al. (PLOS Pathogens. 2012; 8(8):e1002830) using a A/goose/Guangdong/1/96 (H5N1) sequence.

Compounds that inhibit influenza endonuclease may have inhibitory effects on other drug targets owing to the conserved geometry of the catalytic metals in nucleases and polynucleotidyl transferases. Indeed, early influenza endonuclease inhibitors were developed into an anti-AIDS drug targeting HIV-1 integrase (Summa et al., J Med Chem. 2008; 51(18):5843-55). Other viral drug targets with similar geometry at their catalytic cores include but are not limited to: NS5b RNA-dependent RNA polymerase of hepatitis C virus (Summa et al., J Med Chem. 2008; 51(18):5843-55), RNase H of HIV-1 reverse transcriptase (Himmel et al., Structure. 2009; 17(12):1625-35), herpes virus terminase (Nadal et al., Proc Natl Acad Sci USA. 2010; 107(37):16078-83), and SARS coronavirus NTPase/helicase. Two metal chelating compounds have also been found to have antibacterial effects (Drakulié et al., ChemMedChem. 2009; 4(12):1971-75) and inhibit bacterial prenyl transferases specifically (Zhang et al., ACS Med Chem Lett. 2012; 3(5):402-6). In addition to having antiviral and antibacterial effects, two metal chelating agents can have cytotoxic effects on eukaryotic cells. One set of compounds was found to have selective anti-leukemic cytotoxicity by inhibiting a terminal deoxyribonucleotidyl transferase (Locatelli et al., Mol Pharm. 2005; 68(2):538-50). In addition, it has been suggested that administration of D-serine with a D-amino acid oxidase (DAAO) inhibitor could allow for more effective delivery of D-serine to the brain, which could be effective in the treatment of symptoms of schizophrenia. Several compounds related to 3-hydroxypyridin(1H)2-ones and its aza-analogs have recently been reported to have activity as D-amino acid oxidase inhibitors (Hondo, et al., J. Med. Chem. 2012, 56, 3582-3592; Duplantier et al, J. Med. Chem., 2009, 52, 3576-3585).

SUMMARY OF THE INVENTION

Accordingly the invention provides a compound of formula (I):

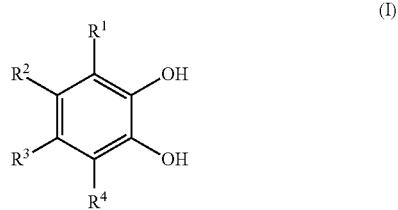

wherein:

$R^1$ is H or $NO_2$;

one of $R^2$ and $R^3$ is $R^a$; and the other of $R^2$ and $R^3$ is phenyl, naphthyl, or a 5-6 membered heteroaryl, wherein any phenyl, naphthyl, and 5-6 membered heteroaryl is optionally substituted with one or more $R^b$;

$R^4$ is H or $(C_1-C_4)$alkyl that is optionally substituted with one or more $R^d$;

$R^a$ is H, halo, aryl, heteroaryl, aryl$(C_1-C_4)$alkyl, heteroaryl$(C_1-C_4)$alkyl, or $(C_1-C_6)$alkyl, wherein any aryl and heteroaryl is optionally substituted with one or more $R^c$, and wherein any $(C_1-C_4)$alkyl and $(C_1-C_6)$alkyl is optionally substituted with one or more $R^k$;

each $R^b$ is independently selected from the group consisting of halo, hydroxy, $(C_1-C_6)$alkyl, $(C_2-C_6)$alkenyl, $(C_2-C_6)$alkynyl, $(C_1-C_6)$alkoxy, cyano, tetrazole, carboxy, phenyl, naphthyl, —$NR^eR^f$, —$C(=O)NR^eR^f$, and nitro, wherein each $(C_1-C_6)$alkyl, $(C_2-C_6)$alkenyl, $(C_2-C_6)$alkynyl, phenyl, naphthyl, and $(C_1-C_6)$alkoxy, are optionally substituted with one or more groups independently selected from halo, hydroxy, —$NR^eR^f$, carboxy, heterocycle, and —$C(=O)NR^eR^f$;

each $R^c$ is independently selected from the group consisting of halo, hydroxy, $(C_1-C_6)$alkyl, $(C_2-C_6)$alkenyl, $(C_2-C_6)$alkynyl, $(C_1-C_6)$alkoxy, cyano, aryl, heteroaryl, and nitro, wherein each $(C_1-C_6)$alkyl, $(C_2-C_6)$alkenyl, $(C_2-C_6)$alkynyl, and $(C_1-C_6)$alkoxy, are optionally substituted with one or more groups independently selected from halo, hydroxy, —$NR^eR^f$, carboxy, heterocycle, and —$C(=O)NR^eR^f$, and wherein any aryl and heteroaryl is optionally substituted with one or more groups independently selected from halo, hydroxy, $(C_1-C_6)$alkyl, $(C_2-C_6)$alkenyl, $(C_2-C_6)$alkynyl, $(C_1-C_6)$alkoxy, cyano, tetrazole, nitro, —$NR^eR^f$, carboxy, heterocycle, and —$C(=O)NR^eR^f$;

each $R^d$ is independently selected from the group consisting of halo, hydroxy, cyano, carboxy, heterocycle, —$NR^eR^f$, and —$C(=O)NR^eR^f$;

each $R^e$ and $R^f$ is independently selected from hydrogen, $(C_1-C_6)$alkyl, and $(C_1-C_6)$alkanoyl: or $R^e$ and $R^f$ together with the nitrogen to which they are attached form a aziridino, azetidino, morpholino, piperazino, pyrrolidino or piperidino; and each $R^k$ is independently selected from the group consisting of hydroxy, $(C_1-C_6)$alkyl carboxy, and —$C(=O)NR^eR^f$, wherein each $(C_1-C_6)$alkyl is optionally substituted with one or more groups independently selected from halo, hydroxy, —$NR^eR^f$, cyano, carboxy, and —$C(=O)NR^eR^f$;

or a salt or prodrug thereof.

The invention also provides a pharmaceutical composition comprising a compound of formula I or a pharmaceutically acceptable salt or prodrug thereof, and a pharmaceutically acceptable excipient.

The invention also provides a method to promote an antiviral effect in an animal (e.g. a human) comprising administering a compound of formula I, or a pharmaceutically acceptable salt or prodrug thereof, to the animal.

The invention also provides a method to inhibit an endonuclease in an animal (e.g. a human) in need of such treatment comprising administering a compound of formula I, or a pharmaceutically acceptable salt or prodrug thereof, to the animal.

The invention also provides a method to inhibit an exonuclease in an animal (e.g. a human) in need of such treatment comprising administering a compound of formula I, or a pharmaceutically acceptable salt or prodrug thereof, to the animal.

The invention also provides a method to treat influenza in an animal (e.g. a human) comprising administering a compound of formula I, or a pharmaceutical salt or prodrug thereof, to the animal.

The invention also provides a method to treat HIV in an animal (e.g. a human) comprising administering a compound of formula I, or a pharmaceutically acceptable salt or prodrug thereof, to the animal.

The invention also provides a method to treat schizophrenia in an animal comprising administering a compound of formula I, or a pharmaceutically acceptable salt or prodrug thereof, and D-serine to the animal.

The invention also provides a compound of formula I, or a pharmaceutically acceptable salt or prodrug thereof for use in medical therapy.

The invention also provides a compound of formula I, or a pharmaceutically acceptable salt or prodrug thereof for the prophylactic or therapeutic treatment of a viral infection.

The invention also provides a compound of formula I, or a pharmaceutically acceptable salt or prodrug thereof for the prophylactic inhibition of an endonuclease.

The invention also provides a compound of formula I, or a pharmaceutically acceptable salt or prodrug thereof for the prophylactic inhibition of an exonuclease.

The invention also provides a compound of formula I, or a pharmaceutically acceptable salt or prodrug thereof for the prophylactic or therapeutic treatment of influenza.

The invention also provides a compound of formula I, or a pharmaceutically acceptable salt or prodrug thereof for the prophylactic or therapeutic treatment of HIV.

The invention also provides a compound of formula I, or a pharmaceutically acceptable salt or prodrug thereof for the prophylactic or therapeutic treatment of schizophrenia when administered with D-serine.

The invention also provides the use of a compound of formula I, or a pharmaceutically acceptable salt or prodrug thereof to prepare a medicament for treating a viral infection in an animal (e.g. a human).

The invention also provides the use of a compound of formula I, or a pharmaceutically acceptable salt or prodrug thereof to prepare a medicament for inhibiting an endonuclease in an animal (e.g. a human).

The invention also provides the use of a compound of formula I, or a pharmaceutically acceptable salt or prodrug thereof to prepare a medicament for inhibiting an exonuclease in an animal (e.g. a human).

The invention also provides the use of a compound of formula I, or a pharmaceutically acceptable salt or prodrug thereof to prepare a medicament for treating influenza in an animal (e.g. a human).

The invention also provides the use of a compound of formula I, or a pharmaceutically acceptable salt or prodrug thereof to prepare a medicament for treating HIV in an animal (e.g. a human).

The invention also provides the use of a compound of formula I, or a pharmaceutically acceptable salt or prodrug thereof to prepare a medicament for treating schizophrenia in an animal (e.g. a human) when administered with D-serine.

The invention also provides processes and intermediates disclosed herein that are useful for preparing a compound of formula I or a salt or prodrug thereof.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heteroaryl of about eight to ten ring atoms comprising one to four heteroatoms each selected from the group consisting of non-peroxide oxygen, sulfur, and N(X).

The term "heterocycle" as used herein refers to a single saturated or partially unsaturated ring or a multiple condensed ring system. The term includes single saturated or partially unsaturated rings (e.g. 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g. ring systems comprising 2, 3 or 4 rings) wherein a single heterocycle ring (as defined above) can be condensed with one or more heterocycles (e.g. decahydronapthyridinyl), carbocycles (e.g. decahydroquinolyl) or aryls. The rings of the multiple condensed ring system can be connected to each other via fused, spiro and bridged bonds when allowed by valency requirements. It is to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g. a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

Prodrugs

In addition to salt forms, the present invention provides compounds which are in a prodrug form. As used herein the term "prodrug" refers to those compounds that undergo chemical changes under physiological conditions to provide the compounds of formula (I) or a salt thereof. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein a free carboxyl group of a compound of formula (I) can be derivatized as an amide or alkyl ester. As another example, a free hydroxy group of a compound of formula (I) can be derivatized as prodrugs by converting the hydroxy group into a group such as, but not limited to, a phosphate ester, hemisuccinate, dimethylaminoacetate, or phosphoryloxymethyloxy-carbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxy group of the hemiacetal form of a carbohydrate).

For additional examples of prodrugs, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191

(1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond is drawn in a non-stereochemical manner (e.g. flat) the atom to which the bond is attached includes all stereochemical possibilities. It is also to be understood that when a bond is drawn in a stereochemical manner (e.g. bold, bold-wedge, dashed or dashed-wedge) the atom to which the stereochemical bond is attached has the stereochemistry as shown unless otherwise noted.

Accordingly, in one embodiment, a compound of the invention may be greater than 50% a single enantiomer. In another embodiment, a compound of the invention may be at least 51% a single enantiomer. In another embodiment, a compound of the invention may be at least 60% a single enantiomer. In another embodiment, a compound of the invention may be at least 70% a single enantiomer. In another embodiment, a compound of the invention may be at least 80% a single enantiomer. In another embodiment, a compound of the invention may be at least 90% a single enantiomer. In another embodiment, a compound of the invention may be at least 95% a single enantiomer. In another embodiment, a compound of the invention may be at least 98% a single enantiomer. In another embodiment, a compound of the invention may be at least 99% a single enantiomer. In another embodiment, a compound of the invention may be greater than 50% a single diastereomer. In another embodiment, a compound of the invention may be at least 51% a single diastereomer. In another embodiment, a compound of the invention may be at least 60% a single diastereomer. In another embodiment, a compound of the invention may be at least 70% a single diastereomer. In another embodiment, a compound of the invention may be at least 80% a single diastereomer. In another embodiment, a compound of the invention may be at least 90% a single diastereomer. In another embodiment, the compounds of the invention are at least 95% a single diastereomer. In another embodiment, a compound of the invention may be at least 98% a single diastereomer. In another embodiment, a compound of the invention may be at least 99% a single diastereomer.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl: $(C_3-C_8)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl, butanoyl, pentanoyl, or hexanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In one embodiment, $R^1$ is H.

In one embodiment, $R^1$ is $NO_2$.

In one embodiment, $R^2$ is phenyl, naphthyl, or a 5-6 membered heteroaryl, wherein any phenyl, naphthyl, and 5-6 membered heteroaryl is substituted with one or more $R^b$.

In one embodiment, $R^2$ is phenyl that is substituted with one or more $R^b$.

In one embodiment, $R^2$ is phenyl that is substituted with tetrazole.

In one embodiment, $R^2$ is

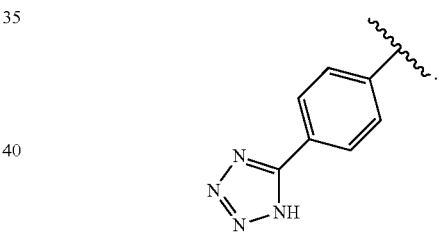

In one embodiment, $R^2$ is $R^a$; and $R^a$ is aryl, heteroaryl, aryl$(C_1-C_4)$alkyl, or heteroaryl$(C_1-C_4)$alkyl, wherein any aryl and heteroaryl is optionally substituted with one or more $R^c$.

In one embodiment, $R^2$ is

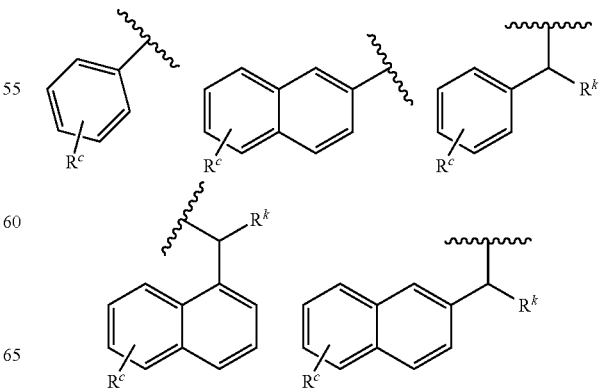

-continued

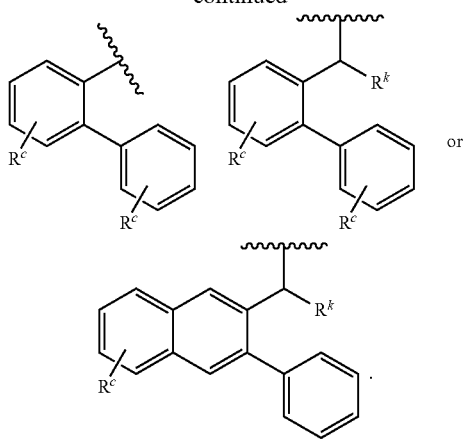

In one embodiment, $R^3$ is $R^a$; and $R^a$ is aryl, heteroaryl, aryl($C_1$-$C_4$)alkyl, or heteroaryl($C_1$-$C_4$)alkyl, wherein any aryl and heteroaryl is optionally substituted with one or more $R^c$.

In one embodiment, $R^3$ is

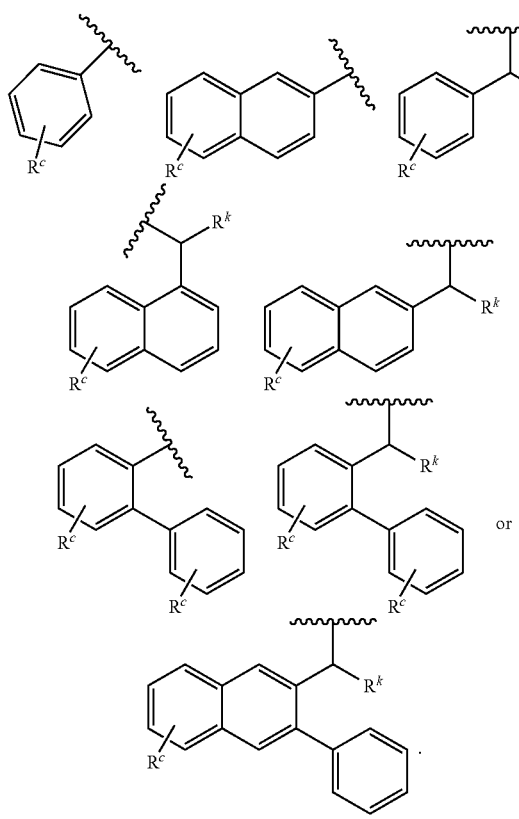

In one embodiment, $R^3$ is phenyl, naphthyl, or a 5-6 membered heteroaryl, wherein any phenyl, naphthyl, and 5-6 membered heteroaryl is substituted with one or more $R^b$.

In one embodiment, $R^3$ is phenyl that is substituted with one or more $R^b$.

In one embodiment, $R^3$ is phenyl that is substituted with tetrazole.

In one embodiment, $R^3$ is

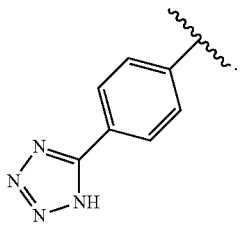 [SMILES: *c1ccc(-c2nnn[nH]2)cc1]

Processes for preparing compounds of formula I are provided as further embodiments of the invention and are illustrated in the following Schemes wherein the meanings of the generic radicals are as given above unless otherwise qualified.

General Scheme 1:

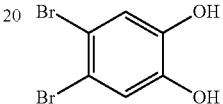

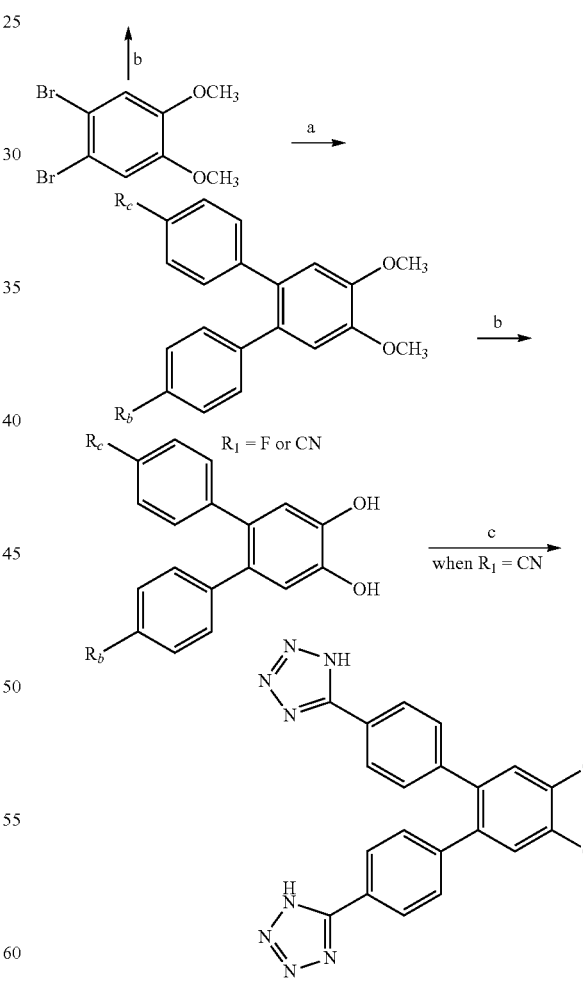

Reagents and conditions:
a 4-R-phenylboronic acid, Pd(PPh$_3$)$_4$/Na$_2$CO$_3$ (for R = CN), Pd(OAc)$_2$/XPhos/K$_2$CO$_3$ (for R = F), dioxane/H$_2$O (2:1), 102° C.;
b BBr$_3$ (1.0 M in DCM), anhydrous DCM;
c NaN$_3$, DMF, cat. AcOH, 135° C..

General Scheme 2:
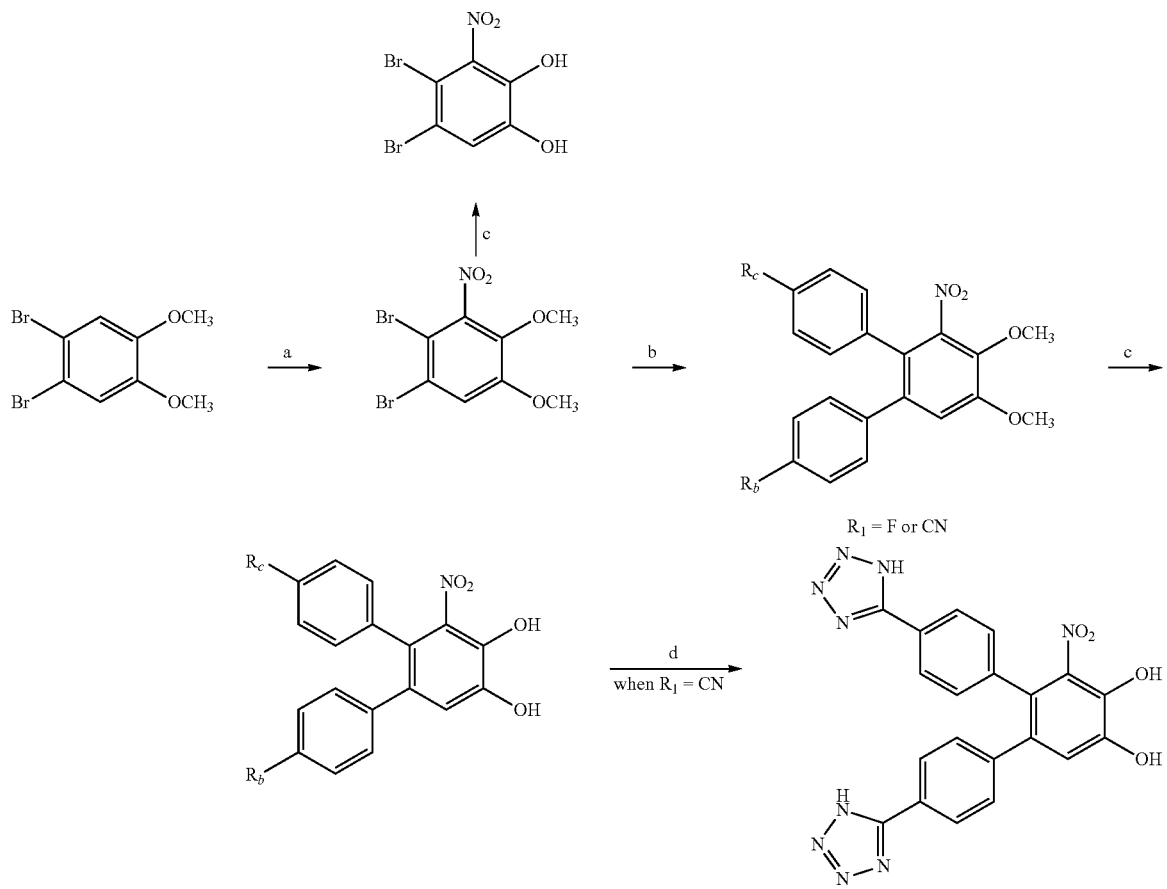
Reagents and conditions:
a tetrabutylammonium nitrate, Tf$_2$O, DCM;
b 4-R-phenylboronic acid, Pd(PPh$_3$)$_4$/Na$_2$CO$_3$ (for R = CN), Pd(OAc)$_2$/XPhos/K$_2$CO$_3$ (for R = F), dioxane/H$_2$O (2:1), 102° C.;
c BBr$_3$ (1.0 M in DCM), anhydrous DCM;
d NaN$_3$, DMF, cat. AcOH, 135° C.
General Scheme 3:
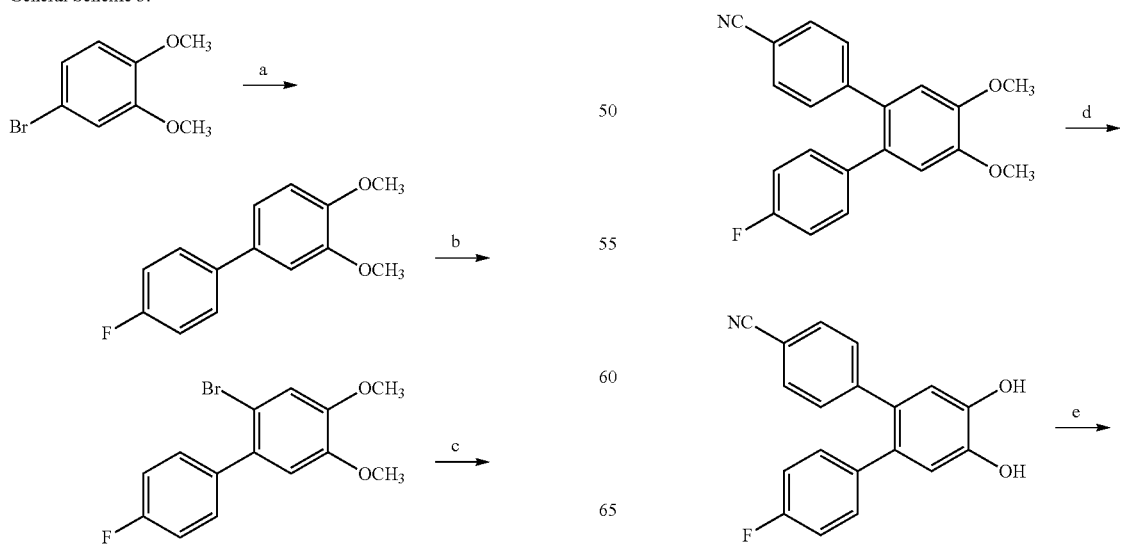

-continued

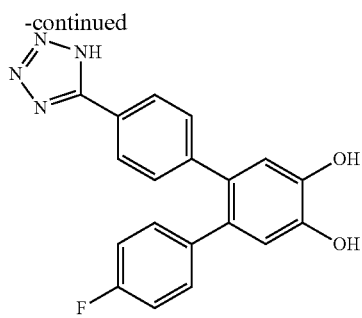

Reagents and conditions:
a 4-fluorophenylboronic acid, Pd(OAc)₂, XPhos, K₂CO₃, dioxane/H₂O (2:1), 102° C.;
b bromine, glacial AcOH, 0° C. to RT;
c 4-cyanophenylboronic acid, Pd(PPh₃)₄, Na₂CO₃, dioxane/H₂O (2:1), 102° C.;
d BBr₃ (1.0M in DCM), anhydrous DCM;
e NaN₃, DMF, cat. AcOH, 135° C.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to an avian or a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, *acacia*, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The compounds can also be administered by inhalation, for example, by oral or nasal inhalation and can be formulated accordingly.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds of the invention are useful for inhibiting endonucleases as well as for inhibiting exonucleases and polynucleotidyl transferases. Thus, the compounds of the invention are useful for treating conditions associated with endonuclease or exonucleases activity, and in particular, conditions wherein inhibition of endonuclease or exonucleases activity is indicated. Additionally, in one embodiment, the invention provides a method to treat a viral infection. Viral infections treatable with compounds of the invention include viruses of the Orthomyxoviridae family (e.g. influenza A, influenza B and influenza C), and viruses of the Arenaviridae and Bunyaviridae families of viruses (e.g. Hantavirus). In one specific embodiment the compounds of the invention are useful for treating viruses associated with "influenza A cap snatching endonucleases." In another specific embodiment the compounds of the invention are useful as anti-HIV integrase and RNase H agents; thus, they are also useful for treating pathological conditions associated with such enzymes.

The invention will now be illustrated by the following non-limiting Examples.

EXAMPLES

Example 1

Preparation of Compound

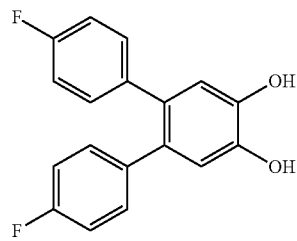 [SMILES: Oc1cc(-c2ccc(F)cc2)c(-c2ccc(F)cc2)cc1O]

To a cooled solution of 4,4''-difluoro-4',5'-dimethoxy-1,1':2',1''-terphenyl (125 mg, 0.38 mmol) in anhydrous DCM (5 mL) was slowly added BBr$_3$ (1.0 M in DCM) (2 mL, 1.92 mmol). Reaction was removed from ice bath and stirred overnight at RT. Solvents were then evaporated. Chromatography using ISCO max gradient 2% MeOH/DCM yielded product as a tan solid (113 mg, quantitative); $^1$H NMR (400 MHz) (CDCl$_3$) δ 6.95-6.91 (m 4H), 6.83-6.79 (m, 6H), 5.21 (bs, 2H); $^{13}$C NMR (100 MHz) (CDCl$_3$) δ 161.6 ($J_{C,F}$=245 Hz), 142.8, 136.8, 132.8, 131.3 ($J_{C,F}$=8 Hz), 117.5, 114.8 ($J_{C,F}$=21 Hz).

The intermediate 4,4''-difluoro-4',5'-dimethoxy-1,1':2',1''-terphenyl was prepared as follows.

a) Preparation of Compound

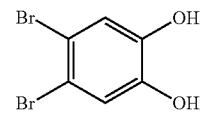

To a cooled solution of 4,5-dibromoveratrole (1 g, 3.38 mmol) in anhydrous DCM (5 mL) was slowly added BBr$_3$ (1.0 M in DCM) (17 mL, 16.9 mmol). Reaction was removed from ice bath and stirred overnight at RT. Solvents were then evaporated. Chromatography using ISCO max gradient 2% MeOH/DCM yielded product as a tan solid (763 mg, 85% yield); $^1$H NMR (400 MHz) (CD$_3$OD) δ 7.04 (s, 2H); $^{13}$C NMR (100 MHz) (CD$_3$OD) δ 147.1, 121.1, 120.8, 114.0.

b) Preparation of 4,4''-Difluoro-4',5'-dimethoxy-1,1': 2',1''-terphenyl

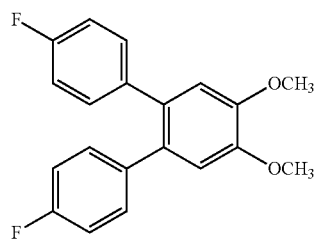 [SMILES: COc1cc(-c2ccc(F)cc2)c(-c2ccc(F)cc2)cc1OC]

A flask containing 4,5-dibromoveratrole (500 mg, 1.69 mmol), 4-fluorophenylboronic acid (946 mg, 6.76 mmol), Pd(OAc)$_2$ (38 mg, 0.169 mmol), XPhos (161 mg, 0.338 mmol), and K$_2$CO$_3$ (1.4 g, 10.1 mmol) was degassed and dioxane (10 mL) and H$_2$O (5 mL) were added. Reaction was refluxed at 102° C. overnight then cooled to RT and diluted with EtOAc. Solution was washed with saturated NaHCO$_3$ solution followed by brine and organic layer was collected, dried over Na$_2$SO$_4$, and concentrated. Chromatography using ISCO max gradient 10% EtOAc/hexane yielded product as a white solid (525 mg, 95% yield); $^1$H NMR (400 MHz) (CDCl$_3$) δ 7.12-7.08 (m, 4H), 6.96-6.91 (m. 6H), 3.97 (s, 6H); $^{13}$C NMR (100 MHz) (CDCl$_3$) δ 161.6 (J$_{C,F}$=244 Hz), 148.4, 137.3 (J$_{C,F}$=3 Hz), 132.1, 131.4 (J$_{C,F}$=8 Hz), 114.9 (J$_{C,F}$=21 Hz), 113.6.

Example 2

Preparation of Compound

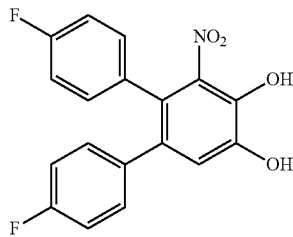 [SMILES: O=[N+]([O-])c1c(O)c(O)cc(-c2ccc(F)cc2)c1-c1ccc(F)cc1]

To a cooled solution of 4,4"-difluoro-4',5'-dimethoxy-3'-nitro-1,1':2',1"-terphenyl (65 mg, 0.175 mmol) in anhydrous DCM (3 mL) was slowly added BBr$_3$ (1.0 M in DCM) (3 mL, 0.88 mmol). Reaction was removed from ice bath and stirred overnight at RT. Solvents were then evaporated. Chromatography using ISCO max gradient 2% MeOH/DCM yielded product as a yellow solid (42 mg, 70% yield); $^1$H NMR (400 MHz) (CD$_3$OD) δ 7.07-7.02 (m, 4H) 6.95-6.88 (m, 5H); $^{13}$C NMR (100 MHz) (CD$_3$OD) δ 164.8-161.9 (m), 147.3, 143.2, 138.6, 137.5 (J$_{C,F}$=4 Hz), 133.3 (J$_{C,F}$=9 Hz), 132.8-132.7 (m), 124.2, 118.6, 115.9-115.5 (m).

The intermediate 4,4"-difluoro-4',5'-dimethoxy-3'-nitro-1,1':2',1"-terphenyl was prepared as follows.

a) Preparation of Compound

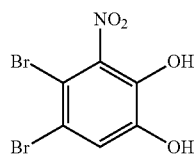

To a cooled solution of 1,2-dibromo-4,5-dimethoxy-3-nitrobenzene (35 mg, 0.1 mmol) in anhydrous DCM (2.5 mL) was slowly added BBr$_3$ (1.0 M in DCM) (0.5 mL, 0.5 mmol). Reaction was removed from ice bath and stirred overnight at RT. Solvents were then evaporated. Chromatography using ISCO max gradient 2% MeOH/DCM yielded product as a tan solid (10 mg, 32% yield); $^1$H NMR (400 MHz) (CD$_3$OD) δ 7.08 (s, 1H); $^{13}$C NMR (100 MHz) (CD$_3$OD) δ 148.6, 140.5, 120.7, 114.3, 104.6.

b) Preparation of Compound

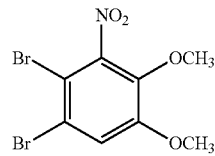

To a flask containing tetrabutylammonium nitrate (305 mg, 1 mmol) in anhydrous DCM (3 mL) at RT was added Tf$_2$O (0.18 mL, 1.05 mmol) resulting in a rise in temperature. The additional needle was then rinsed with additional DCM (2 mL). Reaction was stirred for 1.5 hours at RT and then cooled to −78° C. 4,5-Dibromoveratrole (296 mg, 1 mmol) in anhydrous DCM (3 mL) was then added dropwise, maintaining the temperature below −65° C. Reaction was stirred at −78° C. for an additional 30 minutes and then warmed to RT and stirred for 2 hours. Solution was then washed with saturated NaHCO$_3$ (aqueous pH~8.0) and extracted with additional DCM. Chromatography using ISCO max gradient 10%/EtOAc/hexane yielded product as an off-white solid (215 mg, 63% yield); $^1$H NMR (400 MHz) (CDCl$_3$) δ 7.29 (s, 1H), 3.94 (s, 3H), 3.93 (s, 3H); $^{13}$C NMR (100 MHz) (CDCl$_3$) δ 152.9, 141.1, 119.9, 118.0, 116.0, 105.9, 63.4, 56.7.

c) Preparation of 4,4"-Difluoro-4',5'-dimethoxy-3'-nitro-1,1':2',1"-terphenyl

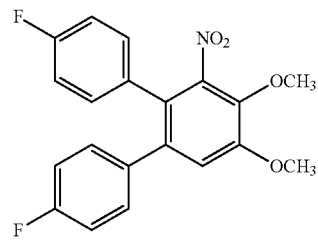 [SMILES: COc1cc(-c2ccc(F)cc2)c(-c2ccc(F)cc2)c([N+](=O)[O-])c1OC]

A flask containing 1,2-dibromo-4,5-dimethoxy-3-nitrobenzene (215 mg, 0.63 mmol), 4-fluorophenylboronic acid (265 mg, 1.89 mmol), Pd(OAc)$_2$ (14 mg, 0.063 mmol), XPhos (60 mg, 0.126 mmol), and K$_2$CO$_3$ (522 mg, 3.78 mmol) was degassed and dioxane (4 mL) and H$_2$O (2 mL) were added. Reaction was heated at 100° C. for 1 hour then cooled to RT and diluted with EtOAc. Solution was washed with saturated NaHCO$_3$ solution followed by brine and organic layer was collected, dried over Na$_2$SO$_4$, and concentrated. Chromatography using ISCO max gradient 10% EtOAc/hexane yielded product as a tan solid (65 mg, 28% yield); $^1$H NMR (400 MHz) (CDCl$_3$) δ 6.97-6.91 (m, 5H), 6.84-6.80 (m, 4H), 3.93 (s, 3H), 3.90 (s, 3H); $^{13}$C NMR (100 MHz) (CDCl$_3$) δ 163.6-160.7 (m), 152.2, 139.7, 137.1, 135.4, 131.9 (J$_{C,F}$=8 Hz), 131.2 (J$_{C,F}$=8 Hz), 130.0, 124.1, 115.5-115.0 (m), 62.2, 56.4.

Example 3

Preparation of Compound 5

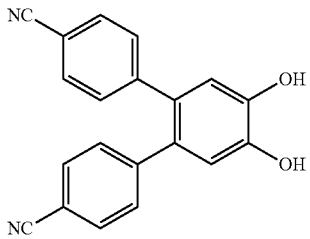 [SMILES: N#Cc1ccc(-c2cc(O)c(O)cc2-c2ccc(C#N)cc2)cc1]

To a cooled solution of 4',5'-dimethoxy-[1,1':2',1''-terphenyl]-4,4''-dicarbonitrile (493 mg, 1.45 mmol) in anhydrous DCM (7 mL) was slowly added BBr$_3$ (1.0 M in DCM) (7.3 mL, 7.25 mmol). Reaction was removed from ice bath and stirred overnight at RT. Solvents were then evaporated. Chromatography using ISCO max gradient 2% MeOH/DCM yielded product as a white solid (104 mg, 23% yield); $^1$H NMR (400 MHz) (DMSO-d$_6$) δ 9.52 (bs, 2H), 7.69 (d, J=8.2 Hz, 4H), 7.20 (d, J=8.2 Hz, 4I-H), 6.85 (s, 2H); $^{13}$C NMR (100 MHz) (DMSO-d$_6$) δ 145.9, 145.7, 132.0, 130.5, 129.5, 118.8, 117.7, 108.9.

The intermediate 4',5'-dimethoxy-[1,1':2',1''-terphenyl]-4,4''-dicarbonitrile was prepared as follows.

a) Preparation of 4',5'-Dimethoxy-[1,1':2',1''-terphenyl]-4,4''-dicarbonitrile

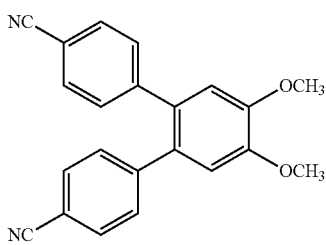 [SMILES: COc1cc(-c2ccc(C#N)cc2)c(-c2ccc(C#N)cc2)cc1OC]

A flask containing 4,5-dibromoveratrole (407 mg, 1.375 mmol), 4-cyanophenylboronic acid (606 mg, 4.125 mmol), Pd(PPh$_3$)$_4$ (159 mg, 0.1375 mmol), and Na$_2$CO$_3$ (729 mg, 6.875 mmol) was degassed and dioxane (6 mL) and H$_2$O (3 mL) were added. Reaction was refluxed at 102° C. overnight then cooled to RT and diluted with EtOAc. Solution was washed with saturated NaHCO$_3$ solution followed by brine and organic layer was collected, dried over Na$_2$SO$_4$, and concentrated. Chromatography using ISCO max gradient 50% EtOAc/hexane yielded product as a light yellow solid (467 mg, quantitative); $^1$H NMR (400 MHz) (CDCl$_3$) δ 7.46-7.44 (m, 4H), 7.14-7.12 (m, 4H), 6.83 (s, 2H), 3.89 (s, 6H); $^{13}$C NMR (100 MHz) (CDCl$_3$) δ 149.4, 145.6, 132.0, 131.3, 130.6, 118.7, 113.5, 110.6, 56.2.

Example 4

Preparation of Compound

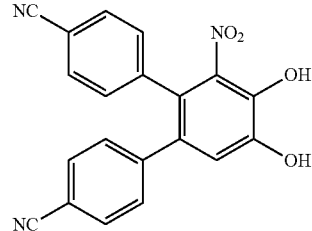 [SMILES: N#Cc1ccc(-c2cc(O)c(O)c([N+](=O)[O-])c2-c2ccc(C#N)cc2)cc1]

To a cooled solution of 4',5' dimethoxy-3'-nitro-[1,1':2',1''-terphenyl]-4,4''-dicarbonitrile (130 mg, 0.338 mmol) in anhydrous DCM (4 mL) was slowly added BBr$_3$ (1.0 M in DCM) (1.35 mL. 1.35 mmol). Reaction was removed from ice bath and stirred overnight at RT. Solvents were then evaporated. Chromatography using ISCO max gradient 2% MeOH/DCM yielded product as a yellow solid (67 mg, 56% yield); $^1$H NMR (400 MHz) (CD$_3$OD) δ 7.60-7.55 (m, 4H), 7.27-7.22 (m, 4H), 7.01 (s, 1H); $^{13}$C NMR (100 MHz) (CD$_3$OD) δ 148.3, 145.9, 141.5, 133.0, 132.9, 132.6, 131.9, 123.5, 119.4, 119.3, 118.5, 112.8, 111.8.

The intermediate 4',5'-dimethoxy-3'-nitro-[1,1':2',1''-terphenyl]-4,4''-dicarbonitrile was prepared as follows.

a) Preparation of 4',5'-Dimethoxy-3'-nitro-[1,1':2',1''-terphenyl]-4,4''-dicarbonitrile

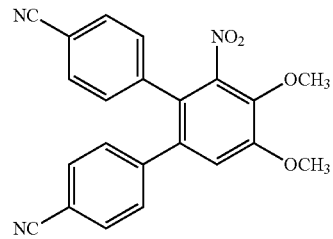 [SMILES: COc1cc(-c2ccc(C#N)cc2)c(-c2ccc(C#N)cc2)c([N+](=O)[O-])c1OC]

A flask containing 1,2-dibromo-4,5-dimethoxy-3-nitrobenzene (150 mg, 0.44 mmol), 4-cyanophenylboronic acid (194 mg, 1.32 mmol), Pd(PPh$_3$)$_4$ (51 mg, 0.044 mmol), and Na$_2$CO$_3$ (233 mg, 2.2 mmol) was degassed and dioxane (4 mL) and H$_2$O (2 mL) were added. Reaction was refluxed at 102° C. overnight then cooled to RT and diluted with EtOAc. Solution was washed with saturated NaHCO$_3$ solution followed by brine and organic layer was collected, dried over Na$_2$SO$_4$, and concentrated. Chromatography using ISCO max gradient 50% EtOAc/hexane yielded product as an off-white solid (130 mg, 77% yield); $^1$H NMR (400 MHz) (CDCl$_3$) δ 7.54-7.52 (m, 4H), 7.20-7.15 (m, 4H), 7.04 (s, 2H), 4.03 (s, 3H), 4.01 (s, 3H); $^{13}$C NMR (100 MHz) (CDCl$_3$) δ 153.1, 146.6, 140.7, 138.5, 135.7, 132.2, 132.1, 130.8, 130.3, 123.1, 118.2, 118.1, 115.2, 112.5, 111.7, 62.3, 60.4.

Example 5

Preparation of Compound

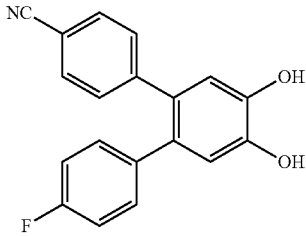 [SMILES: N#Cc1ccc(-c2cc(O)c(O)cc2-c2ccc(F)cc2)cc1]

To a cooled solution of 4"-fluoro-4',5'-dimethoxy-[1,1':2',1"-terphenyl]-4-carbonitrile (80 mg, 0.24 mmol) in anhydrous DCM (3 mL) was slowly added BBr$_3$ (1.0 M in DCM) (1.2 mL, 1.2 mmol). Reaction was removed from ice bath and stirred overnight at RT. Solvents were then evaporated. Chromatography using ISCO max gradient 2% MeOH/DCM yielded product as an off-white solid (50 mg, 68% yield); $^1$H NMR (400 MHz) (CD$_3$OD) δ 7.55-7.53 (m, 2H), 7.24-7.22 (m, 2H), 7.07-7.03 (m, 2H), 6.96-6.92 (m, 2H), 6.86 (s, 1H), 6.68 (s, 1H); $^{13}$C NMR (100 MHz) (CD$_3$OD) δ 148.3, 146.9, 146.3, 138.7, 132.8, 132.7, 131.7, 119.9, 118.7, 118.3, 115.7 ($J_{C,F}$=22 Hz), 110.6.

The intermediate 4"-fluoro-4',5'-dimethoxy-[1,1':2',1"-terphenyl]-4-carbonitrile was prepared as follows.

a) Preparation of Compound

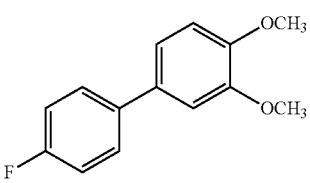 [SMILES: COc1ccc(-c2ccc(F)cc2)cc1OC]

A flask containing 4-bromo-1,2-dimethoxybenzene (2 g, 9.22 mmol), 4-fluorophenylboronic acid (1.55 g, 11 mmol), Pd(OAc)$_2$ (207 mg, 0.922 mmol), XPhos (878 mg, 1.844 mmol), and K$_2$CO$_3$ (3.8 g, 27.66 mmol) was degassed and dioxane (13 mL) and H$_2$O (6.5 mL) were added. Reaction was refluxed at 102° C. overnight then cooled to RT and diluted with EtOAc. Solution was washed with saturated NaHCO$_3$ solution followed by brine and organic layer was collected, dried over Na$_2$SO$_4$, and concentrated. Chromatography using ISCO max gradient 50% EtOAc/hexane yielded product as a white solid (1.35 g, 63% yield); $^1$H NMR (400 MHz) (CDCl$_3$) δ 7.53-7.50 (m, 2H), 7.14-7.07 (m, 4H), 6.95 (d, J=8.2 Hz, 1H), 3.96 (s, 3H), 3.93 (s, 3H); $^{13}$C NMR (100 MHz) (CDCl$_3$) δ 162.2 ($J_{C,F}$=244 Hz), 149.2, 148.7, 137.2 ($J_{C,F}$=4 Hz), 133.3, 128.4 ($J_{C,F}$=8 Hz), 119.3, 115.5 ($J_{C,F}$=21 Hz), 111.6, 110.4, 56.0, 55.9.

b) Preparation of Compound

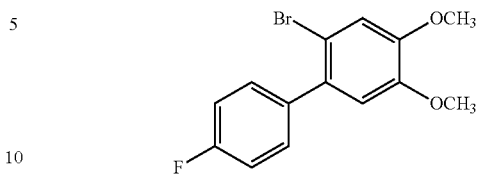

Bromine (0.39 mL, 7.56 mmol) was added dropwise to a solution of 4'-fluoro-3,4-dimethoxy-1,1'-biphenyl (1.35 g, 5.82 mmol) in glacial acetic acid (6 mL). The resulting orange mixture was then stirred at RT overnight. Reaction was then diluted with H$_2$O and extracted with DCM, washed with 10% Na$_2$S$_2$O$_3$ followed by brine. Organic layer was collected, dried over Na$_2$SO$_4$, and concentrated. Chromatography using ISCO max gradient 10% EtOAc/hexane yielded product as a glassy brown solid (1.45 g, 80% yield); $^1$H NMR (400 MHz) (CDCl$_3$) δ 7.39-7.35 (m, 2H), 7.12 (s, 1H), 7.11-7.07 (m, 2H), 6.81 (s, 1H), 3.90 (s, 3H), 3.86 (s, 3H); $^{13}$C NMR (100 MHz) (CDCl$_3$) 162.2 ($J_{C,F}$=245 Hz), 148.9, 148.4, 137.1 ($J_{C,F}$=4 Hz), 133.7, 131.2 ($J_{C,F}$=8 Hz), 115.8, 114.8 ($J_{C,F}$=21 Hz), 113.9, 112.6, 56.2, 56.1.

c) Preparation of 4"-Fluoro-4',5'-dimethoxy-[1,1':2',1"-terphenyl]-4-carbonitrile

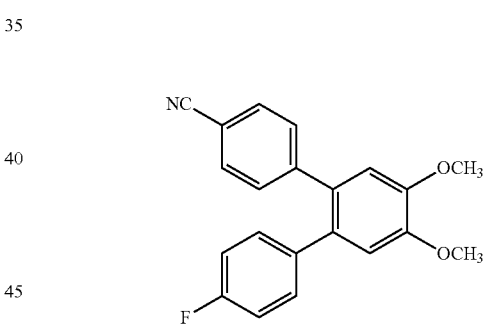

A flask containing 2-bromo-4'-fluoro-4,5-dimethoxy-1,1'-biphenyl (540 mg, 1.74 mmol), 4-cyanophenylboronic acid (306 mg, 2.08 mmol), Pd(PPh$_3$)$_4$ (201 mg, 0.174 mmol), and Na$_2$CO$_3$ (553 mg, 5.22 mmol) was degassed and dioxane (6 mL) and H$_2$O (3 mL) were added. Reaction was refluxed at 102° C. overnight then cooled to RT and diluted with EtOAc. Solution was washed with saturated NaHCO$_3$ solution followed by brine and organic layer was collected, dried over Na$_2$SO$_4$, and concentrated. Chromatography using ISCO max gradient 10% EtOAc/hexane yielded product as a white solid (295 mg, 51% yield); $^1$H NMR (400 MHz) (CDCl$_3$) δ 7.54-7.52 (m, 2H), 7.25-7.23 (m, 2H), 7.09-7.05 (m, 2H), 6.97-6.95 (m, 2H), 6.93 (s, 1H), 6.90 (s, 1H), 3.98 (s, 3H), 3.97 (s, 3H); $^{13}$C NMR (100 MHz) (CDCl$_3$) δ 149.1, 148.7, 146.2, 132.9, 132.4, 131.8, 131.4, 131.3, 131.0, 130.6, 129.7, 115.2 ($J_{C,F}$=21 Hz), 113.79, 113.3, 110.1, 56.2, 56.1.

Example 6

Preparation of Compound

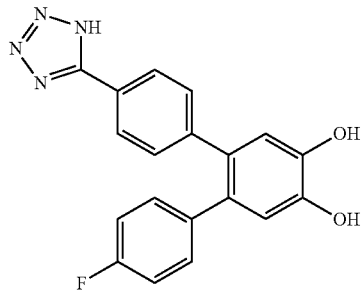 [SMILES: Oc1cc(-c2ccc(F)cc2)c(-c2ccc(-c3nnn[nH]3)cc2)cc1O]

One drop of glacial acetic acid was added to a vial containing 4"-fluoro-4',5'-dihydroxy-[1,1':2',1"-terphenyl]-4-carbonitrile (45 mg, 0.15 mmol) and NaN$_3$ (38 mg, 0.59 mmol) in anhydrous DMF (0.5 mL). The vial was then sealed and heated at 130° C. overnight. Solvents were then evaporated with Kugelrohr and residue was redissolved in a small amount of H$_2$O. A few drops of 10% HCl were then added to crash out solid material which was then filtered. These solids were then suspended in MeOH and filtered again. Filtrate was collected and dried to yield product as a brown solid (14 mg, 27% yield); $^1$H NMR (400 MHz) (CD$_3$OD) δ 7.75 (d, J=7.8 Hz, 4H), 7.11 (d, J=7.8 Hz, 4H), 6.82 (s, 2H).

Example 7

Preparation of Compound

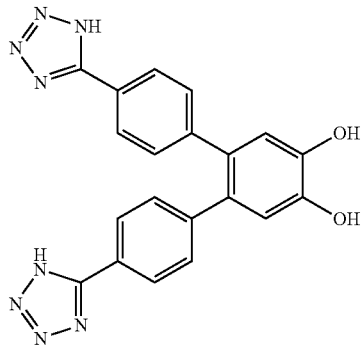 [SMILES: Oc1cc(-c2ccc(-c3nnn[nH]3)cc2)c(-c2ccc(-c3nnn[nH]3)cc2)cc1O]

One drop of glacial acetic acid was added to a vial containing 4',5'-dihydroxy-[1,1':2',1"-terphenyl]-4,4"-dicarbonitrile (25 mg, 0.08 mmol) and NaN$_3$ (42 mg, 0.64 mmol) in anhydrous DMF (0.5 mL). The vial was then sealed and heated at 130° C. overnight. Solvents were then evaporated with Kugelrohr and residue was redissolved in a small amount of H$_2$O. A few drops of 10% HCl were then added to crash out solid material which was then filtered. These solids were then suspended in MeOH and filtered again. Filtrate was collected and dried to yield product as a brown solid (42 mg, 70% yield); $^1$H NMR (400 MHz) (CD$_3$OD) δ 7.75 (d, J=7.8 Hz, 4H), 7.11 (d. J=7.8 Hz, 4H), 6.82 (s, 2H); $^{13}$C NMR (100 MHz) (CD$_3$OD) δ 161.4, 146.2, 144.3, 133.1, 131.5, 127.9, 127.4, 118.6.

The ability of a compound to inhibit endonuclease activity can be evaluated using known assays or using the assay described in Example 36. The novel assay described in Example 8 represents part of the invention.

Example 8

Endonuclease Assay

The PA$_N$ domain has been shown to cleave ssRNA as well as ssDNA. To demonstrate the inhibition of endonuclease cleavage by PA$_N$, a high throughput assay was developed (U.S. patent application Ser. No. 13/554,709). A TaqMan-like oligonucleotide was used containing a 6-carboxy-fluorescein (FAM) fluorophore at the 5'-end followed by 19 nucleotides and a minor groove binding non-fluorescent quencher (MGBNFQ, Applied Biosystems) at the 3'-end. When excited by light at a wavelength of 488 nm, MGB-NFQ quenches the fluorescence of FAM via fluorescence resonance energy transfer. If the endonuclease cleaves the oligonucleotide, the quencher is no longer coupled to the fluorophore, and therefore, FAM fluoresces. This assay can be performed in a high-throughput (e.g. 96 well plate) format. The assay can be used to evaluate the inhibitory characteristics of compounds that are found to bind PA$_N$ and to screen libraries of drug-like compounds. The assay uses the probe 6FAM-TGGCAATATCAGCTCCACA-MGB-NFQ (SEQ ID NO: 1)

The assay can be performed in a 40 μl reaction volume with 50 mM Tris pH 7.5, 50 mM NaCl, 1 mM MgSO$_4$, 0.5 mM MnSO$_4$, 1 mM DTT, 0.75 mM CHAPS, 50 nM probe, and 25 nM endonuclease.

The reaction mixture is set up as a master mix with the buffer, probe, and protein on ice. The inhibitor is then added to a maximum DMSO concentration of 2.5% (v/v) and serial dilutions are made on ice. Varioskan Fluorometer (Thermo Scientific), set to an excitation of 488 nm and emission of 518 nm, is used to measure the fluorescence of the samples at 37 degrees Celsius. Fluorescence is measured at various time points (5, 120, and 240 minutes) during the 37 degrees Celsius incubation. Activity/inhibition is calculated based on the change in fluorescence over time using Prism Graphpad non-linear regression analysis.

Data for representative compounds of formula I in the endonuclease inhibition assay described above is provided in the following table.

| Example # | Structure | IC$_{50}$ (μM) |
|---|---|---|
| 1 | ![structure] | 0.390 |
| 2 | ![structure] | 0.434 |

-continued

| Example # | Structure | IC$_{50}$ (µM) |
|---|---|---|
| 3 | (structure) | 0.395 |
| 4 | (structure) | 0.194 |
| 5 | (structure) | 0.290 |
| 6 | (structure) | 0.425 |
| 7 | (structure) | 0.847 |

The antiviral activity of a compound of the invention can be evaluated using the assay described in Example 9.

Example 9

Antiviral Activity

Anti-influenza activity of the compounds can be tested by plaque assay. Monolayers of Madin-Darby canine kidney (MDCK) cells are inoculated with diluted influenza A virus and allowed to be absorbed for 1 hour. The inoculum is removed and the cells are washed twice with PBS before being covered with agar medium containing minimal essential medium with 0.9% low melting temperature agarose, 4% BSA, 2 mM L-glutamine, 2 mM MEM vitamin (Gibco), and antibiotic antimycotic solution (10 units penicillin, 10 µg streptomycin, and 0.25 µg amphotericin B per mL), 1 µg mL-1 tosyl phenylalanyl chloromethyl ketone (TPCK) trypsin, and compound (at least 10 concentrations of each compound done in triplicate). After 3-4 days a second overlay of agar, containing crystal violet, is added to allow plaque counting. IC50 values are then calculated using Graphpad Prism using a 4-parameter equation.

Example 10

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |

| | |
|---|---|
| 0.1N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to promote an antiviral effect in an animal comprising administering a compound of formula I:

(I)

wherein:
R$^1$ is H or NO$_2$;
one of R$^2$ and R$^3$ is R$^a$; and the other of R$^2$ and R$^3$ is phenyl, naphthyl, or a 5-6 membered heteroaryl, wherein any phenyl, naphthyl, and 5-6 membered heteroaryl is optionally substituted with one or more R$^b$;
R$^4$ is H or (C$_1$-C$_4$)alkyl that is optionally substituted with one or more R$^d$;
R$^a$ is halo, aryl, heteroaryl, aryl(C$_1$-C$_4$)alkyl, or heteroaryl (C$_1$-C$_4$)alkyl, wherein any aryl and heteroaryl is optionally substituted with one or more R$^c$, and wherein any (C$_1$-C$_4$)alkyl is optionally substituted with one or more R$^k$;
each R$^b$ is independently selected from the group consisting of halo, hydroxy, (C$_1$-C$_6$)alkyl, (C$_2$-C$_6$)alkenyl, (C$_2$-C$_6$)alkynyl, (C$_1$-C$_6$)alkoxy, cyano, tetrazole, carboxy, phenyl, naphthyl, —NR$^e$R$^f$, —C(=O)NR$^e$R$^f$, and nitro, wherein each (C$_1$-C$_6$)alkyl, (C$_2$-C$_6$)alkenyl, (C$_2$-C$_6$)alkynyl, phenyl, naphthyl, and (C$_1$-C$_6$)alkoxy, are optionally substituted with one or more groups independently selected from halo, hydroxy, —NR$^e$R$^f$, carboxy, heterocycle, and —C(=O)NR$^e$R$^f$;

each R$^c$ is independently selected from the group consisting of halo, hydroxy, (C$_1$-C$_6$)alkyl, (C$_2$-C$_6$)alkenyl, (C$_2$-C$_6$)alkynyl, (C$_1$-C$_6$)alkoxy, cyano, aryl, heteroaryl, and nitro, wherein each (C$_1$-C$_6$)alkyl, (C$_2$-C$_6$)alkenyl, (C$_2$-C$_6$)alkynyl, and (C$_1$-C$_6$)alkoxy, are optionally substituted with one or more groups independently selected from halo, hydroxy, carboxy, heterocycle, and —C(=O)NR$^e$R$^f$, and wherein any aryl and heteroaryl is optionally substituted with one or more groups independently selected from halo, hydroxy, (C$_1$-C$_6$)alkyl, (C$_2$-C$_6$)alkenyl, (C$_2$-C$_6$)alkynyl, (C$_1$-C$_6$)alkoxy, cyano, tetrazole, nitro, —NR$^e$R$^f$, carboxy, heterocycle, and —C(=O)NR$^e$R$^f$;

each R$^d$ is independently selected from the group consisting of halo, hydroxy, cyano, carboxy, heterocycle, —NR$^e$R$^f$, and —C(=O)NR$^e$R$^f$;

each R$^e$ and R$^f$ is independently selected from hydrogen, (C$_1$-C$_6$)alkyl, and (C$_1$-C$_6$)alkanoyl; or R$^e$ and R$^f$ together with the nitrogen to which they are attached form a aziridino, azetidino, morpholino, piperazino, pyrrolidino or piperidino; and each R$^k$ is independently selected from the group consisting of hydroxy, (C$_1$-C$_6$)alkyl, carboxy, and —C(=O)NR$^e$R$^f$, wherein each (C$_1$-C$_6$)alkyl is optionally substituted with one or more groups independently selected from halo, hydroxy, —NR$^e$R$^f$, cyano, carboxy, and —C(=O)NR$^e$R$^f$;

or a pharmaceutically acceptable salt or prodrug thereof, to the animal.

2. The method of claim 1 wherein R$^1$ is H.

3. The method of claim 1 wherein R$^1$ is NO$_2$.

4. The method of claim 1 wherein R$^2$ is phenyl, naphthyl, or a 5-6 membered heteroaryl, wherein any phenyl, naphthyl, and 5-6 membered heteroaryl is substituted with one or more R$^b$.

5. The method of claim 1 wherein R$^2$ is phenyl that is substituted with one or more R$^b$.

6. The method of claim 1 wherein R$^2$ is R$^a$; and R$^a$ is aryl, heteroaryl, aryl(C$_1$-C$_4$)alkyl, or heteroaryl(C$_1$-C$_4$)alkyl, wherein any aryl and heteroaryl is optionally substituted with one or more R$^c$.

7. The method of claim 1 wherein $R^2$ is

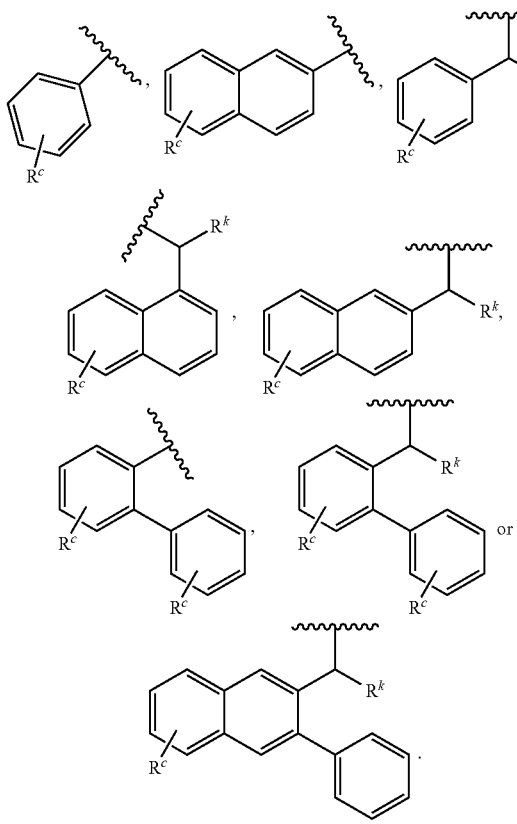

8. The method of claim 1 wherein $R^3$ is $R^a$; and $R^a$ is aryl, heteroaryl, aryl($C_1$-$C_4$)alkyl, or heteroaryl($C_1$-$C_4$)alkyl, wherein any aryl and heteroaryl is optionally substituted with one or more $R^c$.

9. The method of claim 1 wherein $R^3$ is

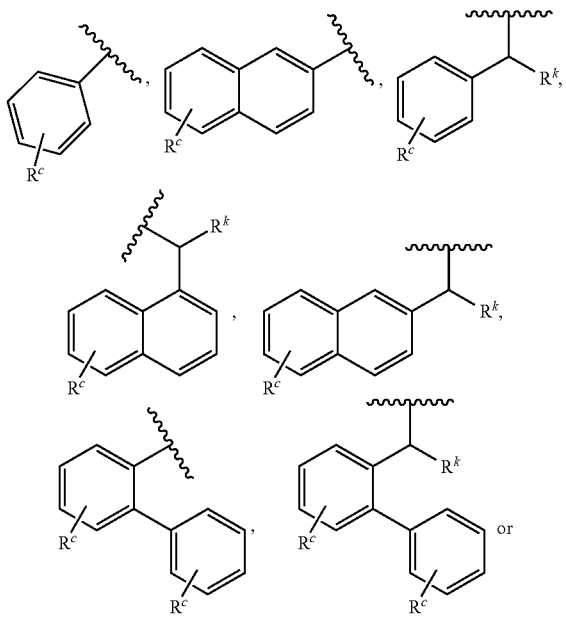

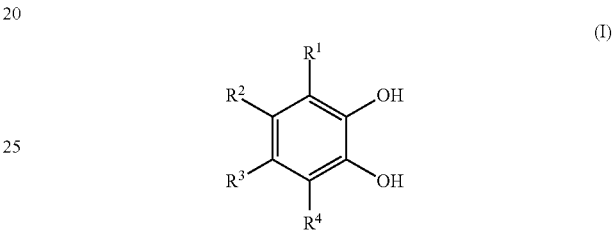

10. The method of claim 1 wherein $R^3$ is phenyl, naphthyl, or a 5-6 membered heteroaryl, wherein any phenyl, naphthyl, and 5-6 membered heteroaryl is substituted with one or more $R^b$.

11. The method of claim 1 wherein $R^3$ is phenyl that is substituted with one or more $R^b$.

12. A method to promote an antiviral effect in an animal comprising administering a compound of formula I:

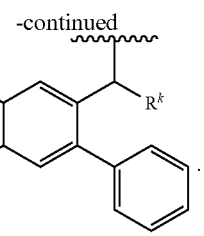

(I)

wherein:
$R^1$ is H or $NO_2$;
$R^3$ is $R^a$; and $R^2$ is phenyl that is substituted with tetrazole;
$R^4$ is H or ($C_1$-$C_4$)alkyl that is optionally substituted with one or more $R^d$;
$R^a$ is H, halo, aryl, heteroaryl, aryl($C_1$-$C_4$)alkyl, heteroaryl($C_1$-$C_4$)alkyl, or ($C_1$-$C_6$)alkyl, wherein any aryl and heteroaryl is optionally substituted with one or more $R^c$, and wherein any ($C_1$-$C_4$)alkyl and ($C_1$-$C_6$) alkyl is optionally substituted with one or more $R^k$;
each $R^c$ is independently selected from the group consisting of halo, hydroxy, ($C_1$-$C_6$)alkyl, ($C_2$-$C_6$)alkenyl, ($C_2$-$C_6$)alkynyl, ($C_1$-$C_6$)alkoxy, cyano, aryl, heteroaryl, and nitro, wherein each ($C_1$-$C_6$)alkyl, ($C_2$-$C_6$)alkenyl, ($C_2$-$C_6$)alkynyl, and ($C_1$-$C_6$)alkoxy, are optionally substituted with one or more groups independently selected from halo, hydroxy, —$NR^eR^f$, carboxy, heterocycle, and —C(=O)$NR^eR^f$, and wherein any aryl and heteroaryl is optionally substituted with one or more groups independently selected from halo, hydroxy, ($C_1$-$C_6$)alkyl, ($C_2$-$C_6$)alkenyl, ($C_2$-$C_6$)alkynyl, ($C_1$-$C_6$)alkoxy, cyano, tetrazole, nitro, —$NR^eR^f$, carboxy, heterocycle, and —C(=O)$NR^eR^f$;
each $R^d$ is independently selected from the group consisting of halo, hydroxy, cyano, carboxy, heterocycle, —$NR^eR^f$, and —C(=O)$NR^eR^f$;
each $R^e$ and $R^f$ is independently selected from hydrogen, ($C_1$-$C_6$)alkyl, and ($C_1$-$C_6$)alkanoyl; or $R^e$ and $R^f$ together with the nitrogen to which they are attached form a aziridino, azetidino, morpholino, piperazino, pyrrolidino or piperidino; and
each $R^k$ is independently selected from the group consisting of hydroxy, ($C_1$-$C_6$)alkyl, carboxy, and —C(=O)$NR^eR^f$, wherein each ($C_1$-$C_6$)alkyl is optionally substituted with one or more groups independently selected from halo, hydroxy, —$NR^eR^f$, cyano, carboxy, and —C(=O)$NR^eR^f$;

or a pharmaceutically acceptable salt or prodrug thereof, to the animal.

13. A method to promote an antiviral effect in an animal comprising administering a compound of formula I:

(I)

wherein:
$R^1$ is H or $NO_2$;
$R^3$ is $R^a$; and $R^2$ is

;

$R^4$ is H or $(C_1-C_4)$alkyl that is optionally substituted with one or more $R^d$;
$R^a$ is H, halo, aryl, heteroaryl, aryl$(C_1-C_4)$alkyl, heteroaryl$(C_1-C_4)$alkyl, or $(C_1-C_6)$alkyl, wherein any aryl and heteroaryl is optionally substituted with one or more $R^c$, and wherein any $(C_1-C_4)$alkyl and $(C_1-C_6)$alkyl is optionally substituted with one or more $R^k$;
each $R^c$ is independently selected from the group consisting of halo, hydroxy, $(C_1-C_6)$alkyl, $(C_2-C_6)$alkenyl, $(C_2-C_6)$alkynyl, $(C_1-C_6)$alkoxy, cyano, aryl, heteroaryl, and nitro, wherein each $(C_1-C_6)$alkyl, $(C_2-C_6)$alkenyl, $(C_2-C_6)$alkynyl, and $(C_1-C_6)$alkoxy, are optionally substituted with one or more groups independently selected from halo, hydroxy, —$NR^eR^f$, carboxy, heterocycle, and —C(=O)$NR^eR^f$, and wherein any aryl and heteroaryl is optionally substituted with one or more groups independently selected from halo, hydroxy, $(C_1-C_6)$alkyl, $(C_2-C_6)$alkenyl, $(C_2-C_6)$alkynyl, $(C_1-C_6)$alkoxy, cyano, tetrazole, nitro, —$NR^eR^f$, carboxy, heterocycle, and —C(=O)$NR^eR^f$;
each $R^d$ is independently selected from the group consisting of halo, hydroxy, cyano, carboxy, heterocycle, —$NR^eR^f$, and —C(=O)$NR^eR^f$;
each $R^e$ and $R^f$ is independently selected from hydrogen, $(C_1-C_6)$alkyl, and $(C_1-C_6)$alkanoyl; or $R^e$ and $R^f$ together with the nitrogen to which they are attached form a aziridino, azetidino, morpholino, piperazino, pyrrolidino or piperidino; and
each $R^k$ is independently selected from the group consisting of hydroxy, $(C_1-C_6)$alkyl, carboxy, and —C(=O)$NR^eR^f$, wherein each $(C_1-C_6)$alkyl is optionally substituted with one or more groups independently selected from halo, hydroxy, —$NR^eR^f$, cyano, carboxy, and —C(=O)$NR^eR^f$;
or a pharmaceutically acceptable salt or prodrug thereof, to the animal.

14. A method to promote an antiviral effect in an animal comprising administering a compound of formula I:

(I)

wherein:
$R^1$ is H or $NO_2$;
$R^2$ is $R^a$; and $R^3$ is phenyl that is substituted with tetrazole;
$R^4$ is H or $(C_1-C_4)$alkyl that is optionally substituted with one or more $R^d$;
$R^a$ is H, halo, aryl, heteroaryl, aryl$(C_1-C_4)$alkyl, heteroaryl$(C_1-C_4)$alkyl, or $(C_1-C_6)$alkyl, wherein any aryl and heteroaryl is optionally substituted with one or more $R^c$, and wherein any $(C_1-C_4)$alkyl and $(C_1-C_6)$alkyl is optionally substituted with one or more $R^k$;
each $R^c$ is independently selected from the group consisting of halo, hydroxy, $(C_1-C_6)$alkyl, $(C_2-C_6)$alkenyl, $(C_2-C_6)$alkynyl, $(C_1-C_6)$alkoxy, cyano, aryl, heteroaryl, and nitro, wherein each $(C_1-C_6)$alkyl, $(C_2-C_6)$alkenyl, $(C_2-C_6)$alkynyl, and $(C_1-C_6)$alkoxy, are optionally substituted with one or more groups independently selected from halo, hydroxy, —$NR^eR^f$, carboxy, heterocycle, and —C(=O)$NR^eR^f$, and wherein any aryl and heteroaryl is optionally substituted with one or more groups independently selected from halo, hydroxy, $(C_1-C_6)$alkyl, $(C_2-C_6)$alkenyl, $(C_2-C_6)$alkynyl, $(C_1-C_6)$alkoxy, cyano, tetrazole, nitro, —$NR^eR^f$, carboxy, heterocycle, and —C(=O)$NR^eR^f$;
each $R^d$ is independently selected from the group consisting of halo, hydroxy, cyano, carboxy, heterocycle, —$NR^eR^f$, and —C(=O)$NR^eR^f$;
each $R^e$ and $R^f$ is independently selected from hydrogen, $(C_1-C_6)$alkyl, and $(C_1-C_6)$alkanoyl; or $R^e$ and $R^f$ together with the nitrogen to which they are attached form a aziridino, azetidino, morpholino, piperazino, pyrrolidino or piperidino; and
each $R^k$ is independently selected from the group consisting of hydroxy, $(C_1-C_6)$alkyl, carboxy, and —C(=O)$NR^eR^f$, wherein each $(C_1-C_6)$alkyl is optionally substituted with one or more groups independently selected from halo, hydroxy, —$NR^eR^f$, cyano, carboxy, and —C(=O)$NR^eR^f$;
or a pharmaceutically acceptable salt or prodrug thereof, to the animal.

15. A method to promote an antiviral effect in an animal comprising administering a compound of formula I:

(I)

wherein:
R¹ is H or NO₂;
R² is Rᵃ; and R³ is

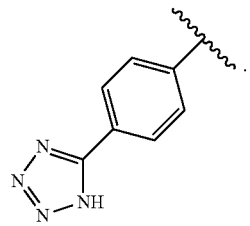 [SMILES: *c1ccc(-c2nnn[nH]2)cc1]

R⁴ is H or (C₁-C₄)alkyl that is optionally substituted with one or more $R^d$;
Rᵃ is H, halo, aryl, heteroaryl, aryl(C₁-C₄)alkyl, heteroaryl(C₁-C₄)alkyl, or (C₁-C₆)alkyl, wherein any aryl and heteroaryl is optionally substituted with one or more $R^c$, and wherein any (C₁-C₄)alkyl and (C₁-C₆)alkyl is optionally substituted with one or more $R^k$;
each $R^c$ is independently selected from the group consisting of halo, hydroxy, (C₁-C₆)alkyl, (C₂-C₆)alkenyl, (C₂-C₆)alkynyl, (C₁-C₆)alkoxy, cyano, aryl, heteroaryl, and nitro, wherein each (C₁-C₆)alkyl, (C₂-C₆)alkenyl, (C₂-C₆)alkynyl, and (C₁-C₆)alkoxy, are optionally substituted with one or more groups independently selected from halo, hydroxy, —NR$^e$R$^f$, carboxy, heterocycle, and —C(=O)NR$^e$R$^f$, and wherein any aryl and heteroaryl is optionally substituted with one or more groups independently selected from halo, hydroxy, (C₁-C₆)alkyl, (C₂-C₆)alkenyl, (C₂-C₆)alkynyl, (C₁-C₆)alkoxy, cyano, tetrazole, nitro, —NR$^e$R$^f$, carboxy, heterocycle, and —C(=O)NR$^e$R$^f$;
each $R^d$ is independently selected from the group consisting of halo, hydroxy, cyano, carboxy, heterocycle, —NR$^e$R$^f$, and —C(=O)NR$^e$R$^f$;
each R$^e$ and R$^f$ is independently selected from hydrogen, (C₁-C₆)alkyl, and (C₁-C₆)alkanoyl; or R$^e$ and R$^f$ together with the nitrogen to which they are attached form a aziridino, azetidino, morpholino, piperazino, pyrrolidino or piperidino; and
each $R^k$ is independently selected from the group consisting of hydroxy, (C₁-C₆)alkyl, carboxy, and —C(=O)NR$^e$R$^f$, wherein each (C₁-C₆)alkyl is optionally substituted with one or more groups independently selected from halo, hydroxy, —NR$^e$R$^f$, cyano, carboxy, and —C(=O)NR$^e$R$^f$;
or a pharmaceutically acceptable salt or prodrug thereof, to the animal.

16. A method to promote an antiviral effect in an animal comprising administering a compound selected from the group consisting of:

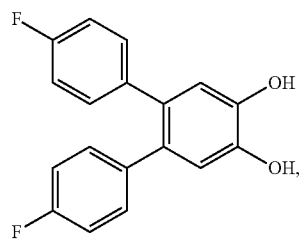

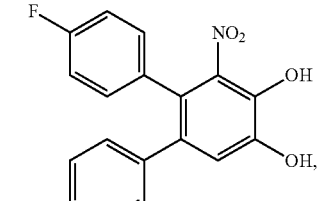

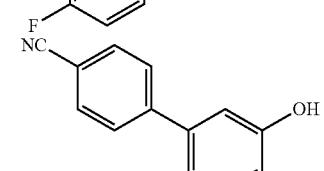

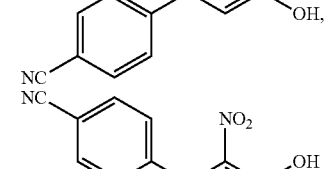

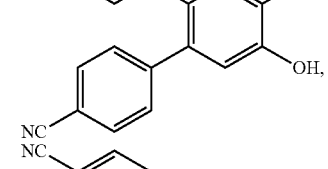

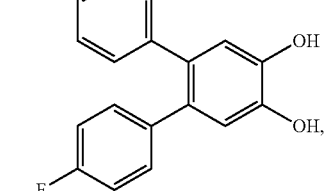

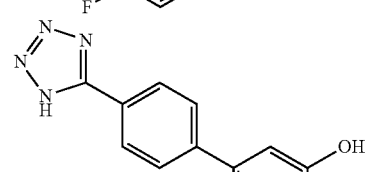

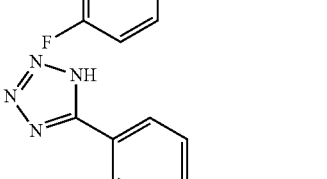 and

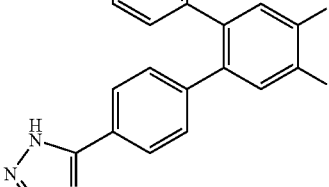

or a pharmaceutically acceptable salt or prodrug thereof is administered.

* * * * *

UNITED STATES PATENT AND TRADEMARK OFFICE
CERTIFICATE OF CORRECTION

PATENT NO. : 9,695,135 B2
APPLICATION NO. : 14/709108
DATED : July 4, 2017
INVENTOR(S) : Edmond J. LaVoie et al.

It is certified that error appears in the above-identified patent and that said Letters Patent is hereby corrected as shown below:

In the Claims

Column 28, Line 15, Claim 1, please delete ", hydroxy, carboxy," and insert
-- , hydroxy, -NR$^e$R$^f$, carboxy, -- therefor.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*